United States Patent
Emrick et al.

(10) Patent No.: US 7,332,609 B2
(45) Date of Patent: Feb. 19, 2008

(54) PEG-SUBSTITUTED PYRIDINE LIGANDS AND RELATED WATER-SOLUBLE CATALYSTS

(75) Inventors: Todd S. Emrick, South Deerfield, MA (US); Kurt Breitenkamp, Northampton, MA (US)

(73) Assignee: University of Massachusetts, Boston, MA (US)

( * ) Notice: Subject to any disclaimer, the term of this patent is extended or adjusted under 35 U.S.C. 154(b) by 149 days.

(21) Appl. No.: 11/254,947

(22) Filed: Oct. 20, 2005

(65) Prior Publication Data

US 2006/0235235 A1    Oct. 19, 2006

Related U.S. Application Data

(60) Provisional application No. 60/620,491, filed on Oct. 20, 2004.

(51) Int. Cl.
*C07F 15/00*    (2006.01)
*C06F 4/44*    (2006.01)
*B01J 31/22*    (2006.01)

(52) U.S. Cl. ............... 548/103; 549/3; 585/531; 502/155; 502/167; 526/141; 526/171; 526/191; 526/204

(58) Field of Classification Search ............... 548/103; 549/3; 502/155, 167; 585/531; 526/141, 526/171, 191, 204
See application file for complete search history.

(56) References Cited

U.S. PATENT DOCUMENTS

| | | | |
|---|---|---|---|
| 5,710,298 A | 1/1998 | Grubbs et al. | |
| 5,939,504 A | 8/1999 | Woodson, Jr. et al. | |
| 6,020,443 A | 2/2000 | Woodson et al. | |
| 6,077,805 A * | 6/2000 | Van Der Schaaf et al. | 502/155 |
| 6,107,420 A | 8/2000 | Grubbs et al. | |
| 6,414,097 B1 * | 7/2002 | Grubbs et al. ............... | 526/160 |
| 6,525,125 B1 | 2/2003 | Giardello et al. | |
| 6,613,910 B2 | 9/2003 | Grubbs et al. | |
| 6,624,265 B2 * | 9/2003 | Grubbs et al. ............... | 526/135 |
| 6,759,537 B2 * | 7/2004 | Grubbs et al. ............... | 548/101 |
| 6,884,859 B2 * | 4/2005 | Grubbs et al. ............... | 526/135 |
| 2003/0055262 A1* | 3/2003 | Grubbs et al. ............... | 548/103 |
| 2003/0069374 A1* | 4/2003 | Grubbs et al. ............... | 526/171 |
| 2006/0178493 A1* | 8/2006 | Maughon et al. ........... | 526/264 |

OTHER PUBLICATIONS

Gallivan, JP; Jordan, JP; and Grubbs, RH; A Neutral, Water-soluble Olefin Metathesis Catalyst Based on a N-heterocyclic Carbene Ligand; Tetrahedron Letters, 2005, 2577-2580, vol. 46.

Breitenkamp, K and Emrick, T; Amphiphilic Ruthenium Benzylidene Metathesis Catalyst with PEG-Substituted Pyridine Ligands; J. Polym. Sci. Part A: Polym. Chem., 2005, 5715-5721, vol. 43.

Skaff, H; Lin, Y; Tangirala, R; Breitenkamp, K; Boker, A; Russel, TP; and Emrick, T; Crosslinked Capsules of Quantum Dots by Interfacial Assembly and Ligand Crosslinking: Adv. Mater. 2005, 2082-2086, vol. 17.

* cited by examiner

*Primary Examiner*—Porfirio Nazario-Gonzalez
(74) *Attorney, Agent, or Firm*—Reinhart Boerner Van Deuren sc

(57) ABSTRACT

Amphiphilic Group VIII metathesis catalysts, as can be used in a range of polymerization reactions and other chemical methodologies.

24 Claims, 3 Drawing Sheets

| Entry[a] | [M]/[Cat 3[b]] | $M_p$[c] | $M_n$[c] | $M_w$[c] | PDI |
|---|---|---|---|---|---|
| 5 | 25 | 79,000 | 67,000 | 90,700 | 1.35 |
| 6 | 50 | 177,400 | 116,200 | 204,400 | 1.76 |

[a] 0.15 M in acidified water (HCl, pH=1.5), 23 °C for 30 min,
[b] Used as 0.015 M solution in acidified water (HCl, pH=1.5),
[c] Determined by GPC in DMF (0.05 M LiBr) relative to poly(methyl methacrylate )standards

PEG-SUBSTITUTED PYRIDINE LIGANDS AND RELATED WATER-SOLUBLE CATALYSTS

This application claims priority from prior provisional application Ser. No. 60/620,491 filed Oct. 20, 2004, the entirety of which is incorporated herein by reference.

The United States government has certain rights to this invention pursuant to Grant Nos. S13200001200000 and N00014-03-1-1000 from the Office of Naval Research and Grant No. DE-FG02-04ER46126 from the Department of Energy, all to the University of Massachusetts.

BACKGROUND OF THE INVENTION

Olefin metathesis is a vital tool in synthetic organic and polymer chemistry. In small molecule chemistry, olefin metathesis represents an effective method to construct elaborate cyclic and heterocyclic molecules, many of which are now being used in pharmaceutical applications. In polymer science, ring-opening and acyclic diene metathesis polymerization provides an effective route to new, highly functional polyolefins. A major limitation of these reactions is a lack of catalyst versatility, particularly concerning catalyst solubility. The vast majority of modern metathesis reactions are performed in organic solvents, typically chlorinated organic solvents. However, as the need for water-based chemistries, materials and processing increases, water-soluble catalysts and their use in polymerization and related synthetic techniques have become an on-going concern in the art.

SUMMARY OF THE INVENTION

In light of the foregoing, it is an object of the present invention to provide metathesis catalyst compounds and/or methods for their use, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is another object of the present invention to provide such compounds directly from commercially-available materials, without resort to multi-step synthetic techniques.

It is an object of the present invention to provide a broad class of compounds having amphiphilic properties and exhibiting catalytic function over a range of chemistries.

It is an object of this invention to provide a catalytic compound heretofore unknown in the art, for use in either aqueous or organic solution, giving good product yield or polymer conversions without long reaction times.

Accordingly, in conjunction with one or more of the preceding objectives, it can be an object of the present invention to provide one or more metathesis catalyst compounds as can be used in conjunction with a range of synthetic organic and polymer chemistries, including but not limited to cross-metathesis reactions, ring-opening metathesis polymerization reactions and the like, as well as for convenient routes to functionalized polyolefins, and related composites and coating materials, not attainable by conventionally synthetic methods.

Other objects, features, benefits and advantages of the present invention will be apparent from this summary and its descriptions of certain embodiments and will be readily apparent to those skilled in the art having knowledge of catalytic compounds and their use in the realm of synthetic organic chemistry. Such objects, features, benefits and advantages will be apparent from the above as taken into conjunction with the accompanying examples, data, figures and all reasonable inferences to be drawn therefrom, alone or with consideration of the references incorporated herein.

In part, the present invention can comprise a compound of a formula (I)

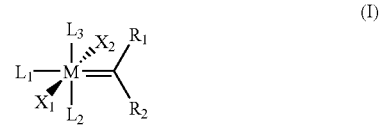

(I)

wherein M can be ruthenium, osmium or another Group VIII metal; $X_1$ and $X_2$ can be independently an anionic ligand, including but not limited to halide ion; $L_1$, $L_2$ and $L_3$ can be independently neutral electron donor ligands, and at least one of $L_1$-$L_3$ can be an N-heterocyclic carbene ligand, and the other L ligand(s) can be independently one of the substituted pyridinyl ligands discussed below; and $R_1$ and $R_2$ can be independently hydrogen, alkyl, substituted alkyl, cyclic alkyl, substituted cyclic alkyl, alkenyl, substituted alkenyl, cyclic alkenyl, substituted cyclic alkenyl, phenyl or substituted phenyl moieties.

As mentioned above, one or two of the neutral electron donor ligands $L_1$-$L_3$ can comprise a pyridinyl moiety substituted with an oligomeric/polymeric component affording amphiphilic properties and function of the sort described herein, such ligands of a formula (II).

(II)

The attached substituent or component (P) of each such pyridine ligand can include, but is not limited to, acyclic ethers and polyethers such as alkyl ethers and alkyl polyethers, the later including poly(ethylene glycol) (PEG), with a molecular weight and degree of oxa substitution as can vary depending upon end use application. Typically, but without limitation, the molecular weight of any such PEG component can range from about 200 to about 5000 or greater. In certain embodiments, where the repeating glycol unit can be represented by $(OCH_2CH_2)_n$, n can range from about 2 to about 10 or up to 100 or greater. Regardless, such a PEG component can, opposite the pyridine terminus be substituted with a functional chain-end moiety such as, but not limited to hydroxy, alkyl, alkoxy (ether), carboxylate, and ammonium or substituted ammonium salts. Various other end/functional groups will be well known to those skilled in the art and made aware of this invention, incorporation of which can be achieved through available synthetic methods either before or after coupling with a suitable pyridinyl or other nitrogenous moiety.

Various other polymeric components can be employed depending upon end use application or compatibility with an associated or predetermined solvent system. Associated polymeric components, without regard as to chain length or molecular weight, include but are not limited to: poly (hexaethylene glycol), poly(hexadecylethylene glycol), poly (F-caprolactone), poly(lactide), poly(glycolide), polyglycidyl, and polypropylene oxide, alone or in combination with one another and/or a PEG component. Accordingly, the present invention includes design, choice or variation of the polymeric component of such a ligand compound depending on a given solvent system. For example, a more hydrophilic polymeric or co-polymeric component could be used in applications involving aqueous systems whereas monomers or polymeric blocks could be included for hydrophobic applications involving organic or mixed solvent systems. Likewise, system solubility can be further modified with ligands comprising multiple polymeric components and/or related substituents. In accordance with this invention, various other pyridinyl ligand components useful in conjunction herewith are described in co-pending application Ser. No. 10/643,015 filed Aug. 18, 2003, the entirety of which is incorporated herein by reference.

With respect to the compounds, composites and/or methods of this invention, the nitrogenous moieties and/or polymeric components can comprise, consist of or consist essentially of any of the aforementioned molecular entities and/or functional groups thereof. Each such moiety or component thereof is distinguishable, characteristically contrasted, and can be practiced in conjunction with the present invention separate and apart from another. Accordingly, it should be understood that the inventive composites, compounds and/or methods, as illustratively disclosed herein, can be practiced or utilized in the absence of any one moiety or component which may or may not be disclosed, referenced or inferred herein, the absence of which may not be specifically disclosed, referenced or inferred herein.

N-heterocyclic carbene (NHC) ligands for metathesis catalysts are well-known in the art. Such a component of catalyst compound I (i.e., one of $L_1$-$L_3$) can be as described more fully in U.S. Pat. No. 6,759,537, the entirety of which is incorporated herein by reference. Without limitation, such components can include the NHC ligands provided in columns 2 and 6-7 of the '537 patent, optionally substituted as shown, each such substituent as can further be substituted with one or more of the moieties and/or functional groups provided therein. In certain embodiments, such a component can comprise a 4,5-dihydroimidazolylidene moiety and can be N-substituted with aryl or substituted aryl moieties. In certain other embodiments, such an N-substituent can be a 2,4,6-trimethylphenyl (i.e., mesityl or mes) moiety.

Likewise, ligands $X_1$ and $X_2$ can, without limitation, include the anionic ligands provided in column 5 of the '537 patent, optionally substituted as shown, each such substituent as can be further substituted with one or more of the moieties and/or functional groups provided therein. In certain embodiments, either or both of $X_1$ and $X_2$ can be halide. In certain other embodiments, one or more of such ligands can be chloride.

Likewise, without limitation, $R_1$ and $R_2$ can be as described in columns 2 and 4-5 of the '537 patent, optionally substituted as shown, each such substituent as can be further substituted with one or more of the moieties and/or functional groups provided therein. In certain embodiments, $R_1$ can be hydrogen and $R_2$ can be selected from $C_1$- about $C_{20}$ alkyl, alkenyl, and aryl moieties, each whether substituted or non-substituted. In certain other embodiments, $R_1$ can be hydrogen and $R_2$ can be phenyl, such that M is coordinated to benzylidene.

Regardless of ligand identity, M can be, as would be understood by those skilled in the art, a Group VIII transition metal including, but not limited to, ruthenium or osmium. (See, e.g. compounds of a formula III, below.) Alternatively, such metal centers can be considered as formally in the +2 oxidation state, having an electron count of 18 and hexacoordinated. In certain non-limiting embodiments, M can be ruthenium or osmium. Accordingly, without limitation, the present invention can relate to such hexacoordinated ruthenium and osmium catalyst compounds, with the understanding that the terms "compound," "catalyst," and "complex." and plurals thereof, can be used interchangeably, herein.

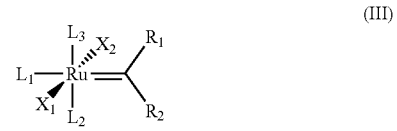

(III)

In part, the present invention can also be directed to a reaction system comprising an amphiphilic hexacoordinated ruthenium or osmium compound of this invention, and at least one alkene compound. Such systems can also comprise one or more fluid medium and/or solvent components, as can be used in conjunction with one or both of such compounds, to facilitate reaction within the content of any particular chemical synthesis or production environment or facility. In certain embodiments, as illustrated below, such a system can comprise two or more acyclic alkene compounds, such that the system can facilitate a cross-metathesis reaction. In certain other embodiments, such a system can comprise cyclic and acyclic alkene compounds, such that the system provides for a ring-opening cross-metathesis reaction.

In certain other embodiments, such a system can comprise a cyclic alkene compound, such that the system provides for a ring-opening metathesis polymerization reaction. In variations of such embodiments, such a system can further comprise a substrate material. As would be understood by those skilled in the art, substituents on such an alkene compound, or such substituents further substituted with one or more functional moieties, can provide for coupling or linking such an alkene compound to a substrate. In certain embodiments, the substrate can be a nanodimensioned particulate, such particulates including, but not limited to, those semi-conductive, luminescent materials known in the art as quantum dots. Such substrates include, but are not limited to, cadmium selenide, cadmium sulfide, cadmium telluride, zinc sulfide, cobalt, and such substrates as can be further provided with a shell, layer or coating thereon (e.g., a cadmium-based nanoparticle, coated with a shell of zinc sulfide or zinc selenide). In such systems, alkene compounds coupled or linked to such a substrate can be cross-linked one with another to provide a corresponding polymeric coating or layer component on the substrate.

As can be related thereto, certain other embodiments of this invention can provide a method of using an N-heterocyclic carbene ruthenium benzylidene catalyst for a ring-opening metathesis reaction in an aqueous medium. Such a method can comprise providing a cyclic alkene compound; and contacting the alkene compound and a corresponding ruthenium catalyst compound of the type described herein, such contact for a time sufficient for reaction of the alkene compound. As demonstrated herein, at least one of the alkene and catalyst compounds can be provided and/or utilized in an aqueous medium. In certain other embodiments, as mentioned above, such an alkene compound can be coupled to a substrate component. Such coupled components can be provided in a substantially hydrophobic medium, such that a catalyst compound in or provided with an aqueous medium can be used to cross-link the substrate-coupled alkene compounds at the media interface. Representative of such embodiments is the operation of a catalyst of this invention on coupled nanoparticulate assemblies or composites at the interface of immiscible fluids, as for instance an oil-water interface where the such nanoparticulate materials can be concentrated.

As discussed above and illustrated elsewhere herein, the pyridine ligands can be polymer-substituted. Accordingly, this invention can also comprise a method of using such ligands to affect the aqueous solubility of an alkylidene/benzylidene carbene metathesis catalyst. Such a method comprises (1) providing a polymer-substituted pyridine ligand component; and (2) contacting the ligand and a Group VIII pentacoordinated or a Group VIII hexacoordinated carbene metathesis catalyst known in the art, such contact sufficient to provide a hexacoordinated Group VIII catalyst compound comprising polymer-substituted pyridine ligand components. The compositional and coordination change afforded by such contact has been found to provide catalyst compounds with improved water solubility and higher metathesis activity than prior water soluble catalysts, as well as amphiphilic properties, as demonstrated below.

DETAILED DESCRIPTIONS OF CERTAIN EMBODIMENTS

Figures 1A, 1B:
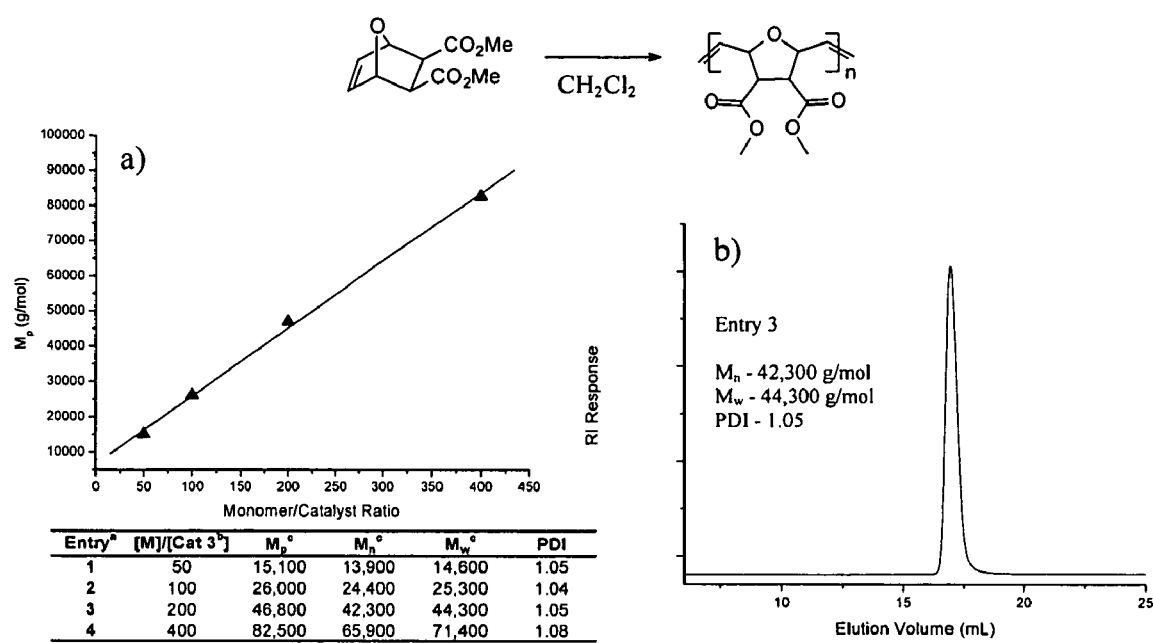
FIGS. 1A-B. A representative ROMP reaction, in accordance with this invention, with GPC analysis of the polymers obtained: (A) Plot of molecular weight versus monomer/catalyst ratio; and (B) GPC chromatogram of entry 3.

Certain embodiments of this invention use poly(ethylene glycol) (PEG)-substituted pyridine molecules as ligands for ruthenium benzylidene catalysts, where the nitrogen of the pyridine group coordinates to the ruthenium metal center of the catalyst. Such PEG-functionalization, or PEGylation, of these ruthenium catalysts gives new water-soluble catalysts that actively polymerize water-soluble cyclic olefins in water. As described below, the synthesis of PEG-substituted pyridines can be accomplished by Mitsunobu coupling of poly(ethylene glycol) diols (i.e., OH at each chain-end) of varying chain length, with 3- or 4-hydroxypyridine. See Scheme 1, below, and various other such substituted pyridine ligands and polymeric components thereof, including but not limited to those described in application Ser. No. 10/643,015 filed Aug. 18, 2003, the entirety of which is incorporated herein by reference. The use of PEG-diols in this coupling step provides a free-hydroxyl group after coordination to the catalyst metal center (i.e., HO-PEG-pyridine-Ru), rendering the new, PEGylated catalysts soluble in water.

Exchange of the tricyclohexylphosphine ligands of the catalyst precursor for these PEG-pyridine ligands can be performed with a 10-fold excess of 1 or 2 (or related compounds with different ethylene glycol chain lengths) in minimal dichloromethane. Removal of dichloromethane in vacuo affords a mixture of 4 and PEG-pyridine starting material as a dark green oil. Dilution of this green oil in water causes precipitation of tricyclohexylphosphine, which is removed easily by centrifugation. Dark green homogeneous solutions of 4 (and e.g. 1 or 2) can then be formed in many solvents, including water, methanol, toluene, and dichloromethane, all of which can be used in meta-thesis chemistry. Alternatively, catalyst compounds of this invention can be prepared and isolated absent excess PEG-pyridine ligand, as shown in several of the following examples.

NMR spectroscopy ($^1$H, $^3$C, and $^{31}$P) performed on a mixture of 4 and 1 (or 2) in D$_2$O confirms the success of the ligand exchange. The $^1$H NMR spectrum of the catalyst mixture taken in CDCl$_3$ shows resonances from $\delta$3.5-3.7 ppm, characteristic of the methylene protons of PEG. A singlet at $\delta$19.2 ppm corresponds to the benzylidene proton. This benzylidene proton is 0.07 ppm downfield from the benzylidene proton of 3.

Scheme 2 illustrates, in accordance with one aspect of this invention, the synthesis of a water-soluble metathesis catalyst by ligand exchange chemistry, using a commercially available pentavalent ruthenium catalyst and an excess of PEG-functionalized pyridine. In important advances from previous water-soluble metathesis catalysts, the compounds of this invention are 1) prepared easily and 2) exhibit markedly enhanced reactivity, due to the nature of the pyridine substituent, and 3) have appreciable solubility in neutral water. While there have been a few reports of metathesis chemistry in aqueous solution, the catalysts utilized in these studies required multistep synthetic procedures. An especially useful benefit of this invention lies in the ability to perform a range of aqueous based metathesis chemistries, such as ring opening metathesis polymerization, ring-closing metathesis and cross-metathesis. For these reactions, catalyst activity is important, since high reaction yield with minimal catalyst loading are preferred. The use of these catalysts has also been demonstrated for the polymerization of polar monomers in water. Again, the ability to carry out polymerizations in entirely aqueous media is advantageous, as organic solvents can be eliminated and post-polymerization purification is minimized.

It should also be noted that the catalysts of this invention are also soluble in a number of organic solvents, due to the amphiphilic nature of the polymeric component (e.g., polyethylene glycol) and its influence on solubility. Thus, the present invention provides a broad class of metathesis catalysts, both in terms of chemistries available and reaction media employed.

Accordingly, Catalyst 4 (Scheme 2) was tested for its ability to polymerize cyclic olefins in dichloromethane and found to successfully polymerize cyclooctene and norbornene to full conversion at room temperature in seconds. The average molecular weights of the polymers produced could be controlled easily by adjustment of the monomer-to-catalyst ratios. FIG. 1 shows GPC data for polymers obtained from exo,exo-5,6-bis(methoxycarbonyl)-7-oxabicyclo[2.2.1] hept-2-ene using catalyst 4 in dichloromethane at various monomer-to-catalyst ratios. In all ratios, the corresponding polyolefin was produced with low PDI values (<1.1) and good control over average molecular weight.

FIG. 1 also shows a plot of molecular weight versus monomer-to-catalyst ratio and a gel permeation chromatograph of the polymer prepared using a monomer-to-catalyst ratio of 200:1. The linear correlation of molecular weight and monomer-to-catalyst ratio, combined with the low PDI values of the resulting polymers, provides evidence for the "living" nature of this ROMP using this PEG-substituted ruthenium benzylidene catalyst. These results are in accord with those from the reports by Grubbs and coworkers on 3-bromopyridine-substituted ruthenium catalysts, and contrast the polymerization prior art catalyst 3, which under similar conditions produces polymers with PDI values greater than 1.5.

To test the metathesis activity of catalyst 4 in a completely aqueous environment, a water-soluble PEG-grafted oxanorbornene (FIG. 2) was synthesized by Mitsunobu coupling of exo-oxanorbornene imide in the presence of excess tetraethylene glycol. In neutral water, catalyst 4 failed to polymerize the tricyclic olefin. However, polymerization occurred in aqueous solution at low pH (2 or lower) as evidenced by a rapid increase in solution viscosity immediately after injection of 4. In this case, the presence of a Bronstead acid may activate the catalyst by protonation of PEG-pyridine ligands, which diminishes their ligation capability and increases the reactivity of catalyst 4 toward cyclic olefins.

Figures 2A, 2B:
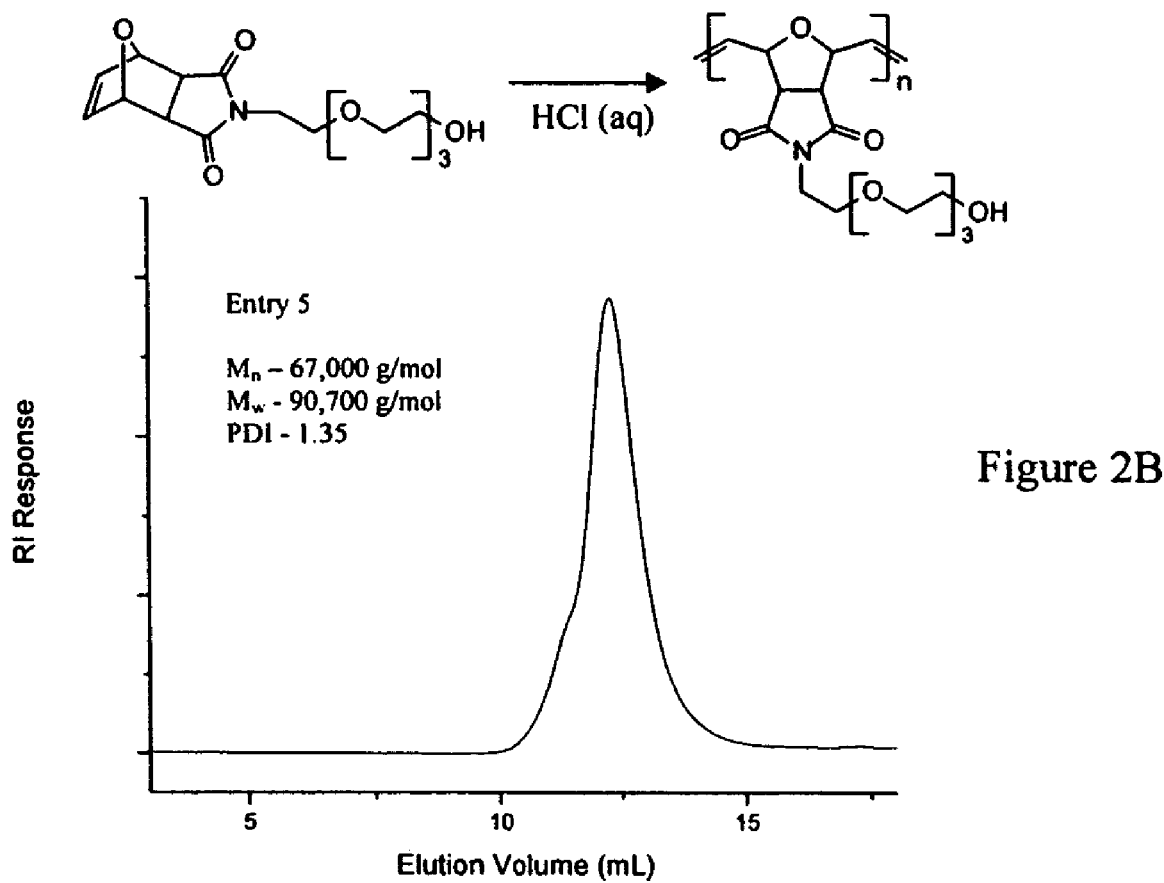
FIGS. 2A-B. Another representative ROMP reaction, in accordance with this invention, with GPC analysis of the polymers obtained with 2A and 2B as described above.

FIG. 2 provides GPC-derived molecular weight data for the polymer prepared by polymerizations that employed various ratios of monomer to catalyst in water at pH 1.5. The average molecular weight of polymer could be adjusted to higher or lower values by variation of the monomer-to-catalyst ratio in aqueous polymerizations using catalyst 4. However, the estimated molecular weights of the polymers obtained, using GPC with DMF as the mobile phase, were not consistent with theoretical estimations. For example, in polymerization using monomer-to-catalyst ratios of 25:1 (entry 5) and 50:1 (entry 6), the polymers obtained had GPC-estimated $M_n$ values of 67,000 and 116,000 g/mol, respectively. Full monomer conversion was confirmed by $^1H$ NMR spectroscopy recorded in $CDCl_3$, wherein resonances at δ6.5 ppm for the cyclic olefin were not observed. Under ideal conditions of quantitative initiation and absence of termination reactions, $M_n$ values of ~10,000 and 20,000 g/mol would have been obtained for entries 5 and 6, respectively. This rather significant discrepancy in theoretical versus experimental molecular weight, along with the relatively broad PDI values (1.3-2.4), suggests that initiation by catalyst 4 under these conditions is incomplete or slow. In contrast, good agreement of theoretical versus experimentally estimated molecular weight (by GPC) was found for the polymerization in dichloromethane.

Relating to certain other embodiments of this invention, molecular monolayers can be constructed on a variety of substrates. As shown herein, when such molecular components or a monolayer thereof bear appropriate functionality, polymerization chemistries can be used to cross-link the components. Relative to flat surfaces or interfaces, the spherical surface of a droplet offers four times the surface area, provides greater access to the surrounding environment, and offers an effective route for encapsulation within a droplet. Nanoparticle assemblies on droplets represent, in many respects, ideal platforms for tuning capsule-environment interactions, as the ligands associated with each nanoparticle provide opportunities for tailored interfacial interactions and chemistries.

A unique aspect associated with interfacial assembly of nanoparticles and fluids is the highly mobile nature of the assembly, which provides rapid diffusion within the interface and fast equilibration of the assembly. For instance, tri-n-octylphosphine oxide (TOPO)-covered CdSe nanoparticles can readily segregate to a toluene/water interface. However, experience with such TOPO-covered CdSe quantum dots reveal this nanoparticle interfacial assembly becomes less stable with increasing temperature (e.g., for effecting reactive chemistry on associated ligands). In this light, the present invention can be seen as an approach to nanoparticle-based materials with improved mechanical integrity.

As demonstrated below, the catalyst compounds of this invention can also be used to effect transformation of interfacial (e.g., fluid-fluid) assemblies to robust nanoparticle capsules and substrate sheets by cross-linking the ligands fixed to a nanoparticle or substrate surface. Success of this invention in such embodiments can be evidenced by operation at room temperature. For instance, nanoparticle assemblies remain intact during the cross-linking process, demonstrating an excellent means of cross-linking nanoparticle assemblies where the nanoparticles are surface-functionalized with cyclic olefins. Previous efforts to cross-link such assemblies presented difficulties associated with the temperatures needed (ca. 60° C.) for the free radical cross-linking method employed. Such elevated temperatures led to some degree of rupture of the capsules due to thermal expansion during cross-linking. In contrast, the metathesis catalysts of this invention are active at room temperature. Moreover, the water-solubility and amphiphilicity of the catalysts provides for cross-linking from the aqueous side of an oil-water interface, and at the interface, and the preparation of well-defined capsules, as polymerization of the excess ligand-covered nanoparticles in the organic phase (i.e., not part of the capsule structure) is precluded. The result is clean cross-linking with high reproducibility and excellent structural integrity enabled by the use of these amphiphilic metathesis catalysts.

More specifically, representative of various other embodiments, the compounds and methods of this invention can be directed toward quantum dots functionalized with cyclic olefin ligands and interfacial cross-linking by ring-opening metathesis polymerization, at room temperature. With reference to examples 4-8 below, norbornene-functionalized CdSe/ZnS core/shell nanoparticles were prepared, found to assemble at an oil-water interface, and utilized for ligand cross-linking.

Application of ring-opening metathesis polymerization was first attempted using Grubb's Generation II catalyst, a representative catalyst of the prior art. Results showed that cross-linking was complicated by the presence of norbornene-functionalized nanoparticles in the continuous toluene phase. The hydrophobic nature of the catalyst led to ring-opening chemistry not specific to the interface, but occurring throughout the interface and the continuous phase to give inter-capsule cross-linked nanoparticles throughout the continuous phase, connected to, and extending outward from, the capsules.

Interfacial cross-linking was improved dramatically by use of an amphiphilic metathesis catalyst compound in this invention, capable of function in both the water phase and at the interface. For instance and without limitation, cross-linking of the nanoparticle assemblies using catalyst 4 (Scheme 2) was performed by mixing an aqueous solution of the catalyst with a toluene solution of norbornene-functionalized CdSe/ZnS core/shell nanoparticles, followed by shaking the mixture vigorously until a cloudy dispersion was obtained. Capsules obtained through this process were allowed to settle in the toluene phase, then collected.

Figure 3A:
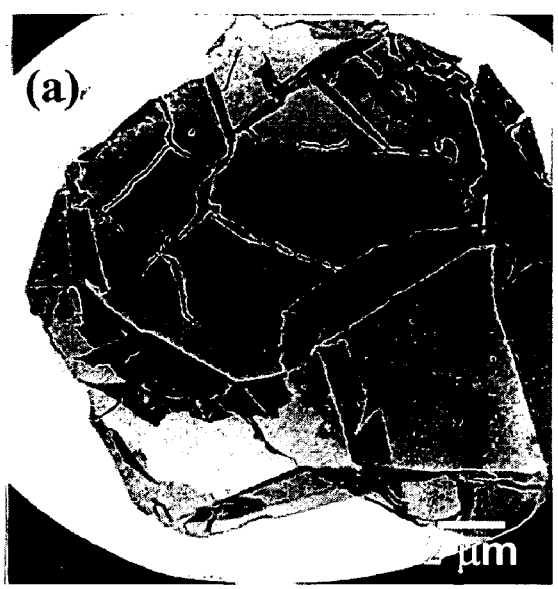
FIGS. 3A-B. TEM images at (A) low magnification of a dried, collapsed nanoparticle capsule; and (B) high resolution showing well dispersed individual nanoparticles.
Figure 3B:
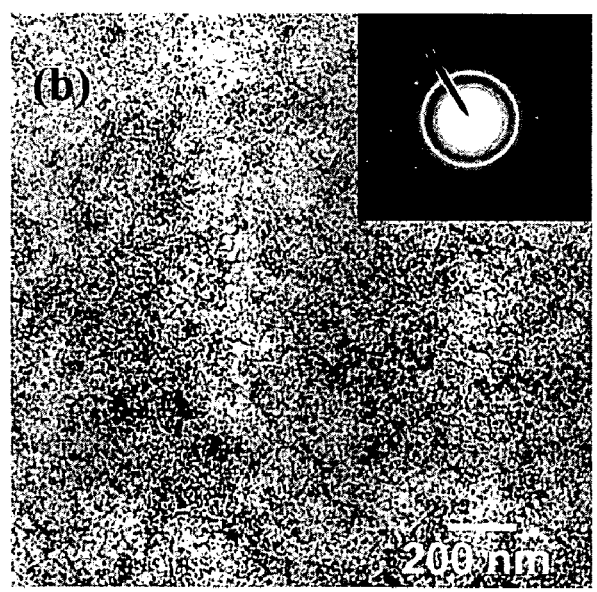

Variation of cross-linking conditions, especially catalyst concentration, revealed differences in capsule morphology. It was found by comparison of fluorescence confocal micrographs that the use of lower catalyst quantities (e.g., 25 as compared to 5 and 1 mg/ml) gave capsules of generally spherical morphology with few defects. Evidence for successful interfacial cross-linking was obtained by visualization of the capsules upon removal of the interface, by washing out the oil and water phases with a single solvent such as methanol. Fluorescence confocal microscopy showed removal of the interface does not disrupt nanoparticle assembly, as is common with uncross-linked assemblies. Rather, droplet structure is maintained, and folds and ridges are observed upon collapse and crumbling of the cross-linked encapsulated layer. (See, FIGS. 3A and 3B)

EXAMPLES OF THE INVENTION

The following non-limiting examples and data illustrate various aspects and features relating to the catalyst compounds and/or methods of the present invention, including use thereof to cross-link nanoparticulate ligand components, as are available through the synthetic methodologies described herein. In comparison with the prior art, the present catalysts and related methods provide results and data which are surprising, unexpected and contrary thereto. While the utility of this invention is illustrated through the use of several catalyst compounds, pyridinyl ligands and associated polymeric components, it will be understood by those skilled in the art that comparable results are obtainable with various other catalyst compounds, pyridinyl moieties and associated polymeric components, as are commensurate with the scope of this invention.

Materials

4-Hydroxypyridine (95%, Aldrich) was passed through a plug of neutral alumina (80/20 $CHCl_3$/MeOH eluent), precipitated into diethyl ether, filtered, and dried in vacuo. Furan (Aldrich) was purified by vacuum distillation over calcium hydride. Tetraethylene glycol (99%) was purchased from Alfa-Aesar and purified by fractional distillation. Tetrahydrofuran (THF) was distilled from sodium benzophenone ketyl. Dichloromethane was washed with concentrated sulfuric acid, dried over magnesium sulfate, and distilled over calcium hydride. Triphenylphosphine (99%), diisopropyl azodicarboxylate (95%), maleic anhydride (99%), maleimide (99%), ethyl vinyl ether (99%), diethylene glycol vinyl ether (98%), and Grubbs' Generation II Catalyst tricyclohexylphosphine [1,3-bis(2,4,6-trimethylphenyl)-4,5-dihydroimidazol-2-ylidene][benzylidine]ruthenium (IV) dichloride were purchased from Aldrich and used as received.

Instrumentation

Nuclear magnetic resonance (NMR) spectroscopy was performed on a Bruker Avance 400 spectrometer (referenced to $CDCl_3$): $^1H$ at 400 MHz and $^{13}C$ at 100 MHz. Molecular weights and polydispersity indices (PDIs) for polymer 5 were estimated by gel permeation chromatography (GPC) in THF (1.0 mL/min) against linear polystyrene standards, using a Knauer HPLC Pump (K-501), Refractive Index detector (K-2301), and three Polymer Laboratories (PL) Mixed D columns (5 μm, 300 mm×7.5 mm). GPC analysis of polymer 7 was performed in dimethylformamide (DMF) (1.0 mL/min) with LiBr (0.05M) at 50° C., using a PL GPC 50 system equipped with two PL Resipore® columns (3 μm, 300 mm×7.5 mm) and referenced against linear poly(methyl methacrylate) standards. HPLC analysis was performed using a Waters Alliance 2695 multi-solvent delivery system equipped with a Waters 2996 photodiode array detector and a Waters XTerra® column (C8, 5 μm, 4.6 mm×150 mm). Attenuated total reflectance-Fourier transform infrared (ATR-FTIR) spectroscopy was performed on a PerkinElmer Spectrum One spectrometer equipped with a Universal Diamond ATR sampling accessory.

Example 1a

Representative synthesis of PEG-pyridine ligand (compound 2 in Scheme 1, n=2). In a dry, round-bottom flask, 4-hydroxypyridine (3.00 g, 31.5 mmol), triphenylphosphine (8.7 g, 33 mmol), and triethylene glycol (14.2 g, 94.6 mmol) were combined and diluted in 100 mL dry THF. The flask containing this mixture was cooled in an ice-water bath (ca. 0° C.), and diisopropylazodicarboxylate (6.40 mL, 33.1 mmol) was injected. After 30 minutes, the ice bath was removed and the mixture was stirred under an atmosphere of nitrogen for 12 hours at room temperature. The mixture was concentrated and dissolved in ether. The product was extracted three times with 1 M $HCl_{(aq)}$. The combined aqueous fractions were treated with aqueous NaOH solution until a pH of 12 was reached. The product was then extracted with chloroform, and the combined organic fractions were dried over $MgSO_4$ and concentrated by rotary evaporation. This crude product was purified by column chromatography over silica gel using chloroform-methanol mixtures to afford 2.9 g of pure 2 (41% yield): $^1H$ NMR ($CDCl_3$) δ 8.26 (d,2H), 6.70 (d, 2H), 4.04 (m, 3H), 3.73 (m, 2H), 3.58 (br m, 8H); $^{13}C$ NMR ($CDCl_3$) δ 164.8, 150.6, 110.3, 72.6, 70.7, 70.2, 69.2, 69.1, 67.1, 61.2; ATR-FTIR 3246, 3036, 2870, 1639, 1591, 1568, 1502, 1454, 1422, 1352, 1284, 1211, 1119, 1051, 1000, 991, 929, 887, 817, 730, 699 $cm^{-1}$.

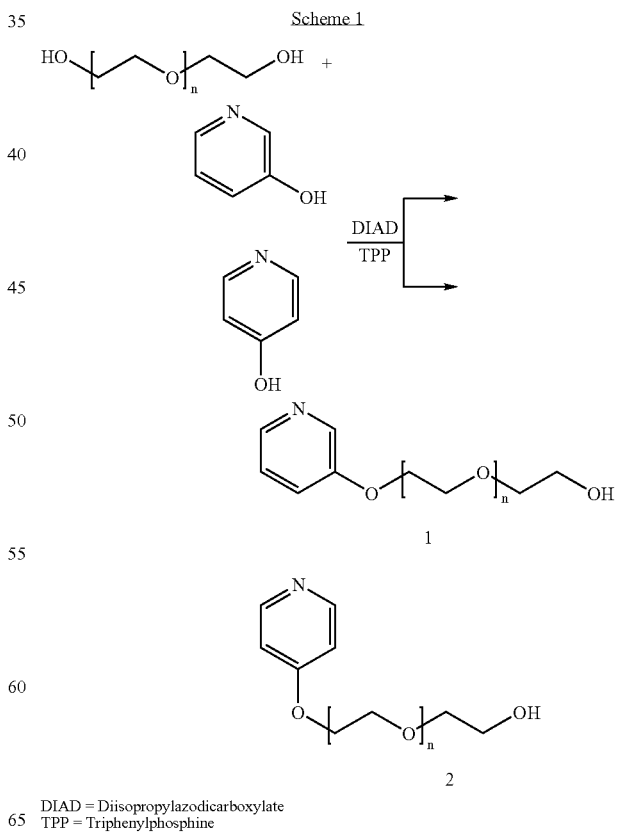

Scheme 1

DIAD = Diisopropylazodicarboxylate
TPP = Triphenylphosphine

Example 1b

With reference to Scheme 1, compound 1 is prepared in an analogous manner from 3-hydroxypyridine. Without limitation, both compounds 1 and 2 can vary by chain length (e.g., n can be from 2 to about 10 or greater), and/or terminal moiety (e.g., amino, alkyl, etc.). See more specifically, examples 1c-1f below.

Example 1c

Synthesis of triethylene glycol substituted pyridine (2-{2-[2-(Pyridin-4-yloxy)-ethoxy]-ethoxy}-ethanol). To a dry, round-bottom flask was added 4-hydroxypyridine (5.00 g, 52.6 mmol), triphenylphosphine (20.68 g, 78.9 mmol), triethylene glycol (23.7 g, 157.8 mmol), and dry THF (125 mL). The mixture was stirred under $N_{2(g)}$ at 0° C., and diisopropyl azodicarboxylate (10.69 mL, 55.2 mmol) was added by addition funnel over 30 minutes. This mixture was stirred for 30 minutes, then the ice bath was removed, and the mixture was stirred under $N_{2(g)}$ for 12 hours at room temperature. The mixture was then concentrated, dissolved in chloroform, and extracted with 1 M $HCl_{(aq)}$. The combined aqueous fractions were treated with a 30 wt % NaOH solution until a pH of 12 was reached. The product was extracted three times with chloroform, and the combined organic fractions were dried over $MgSO_4$ and concentrated. The product was purified first by silica gel chromatography (9:1 $CHCl_3$:MeOH). Next, the product was dissolved in water and passed through Amberlite® IR-120H ion exchange resin (1 M KOH). The product extracted three times with $CHCl_3$, the organic fractions combined, dried over $MgSO_4$, and concentrated to a colorless oil (24% yield): $^1H$ NMR ($CDCl_3$) δ 8.37 (d, 2H), 6.78 (d, 2H), 4.13 (t, 2H), 3.83 (t, 2H), 3.55-3.71 (br m, 8H), 3.08 (br s, 1H); HPLC (acetonitrile, 0.1% trifluoroacetic acid) retention time, 2.121 min.

Example 1d

Synthesis of Tetraethylene Glycol Substituted Pyridine 1-(2-(2-{2-[2-(Pyridin-4-yloxy)-ethoxy]-ethoxy}-ethoxy)-ethanol). To a dry, round-bottomed flask were added 4-hydroxypyridine (3.00 g, 31.6 mmol), triphenylphosphine (9.10 g, 34.7 mmol), tetraethylene glycol (36.8 g, 189 mmol), and dry THF (125 mL). The mixture was stirred under $N_{2(g)}$ at 0° C. (ice-water bath), and diisopropyl azodicarboxylate (6.80 mL, 34.7 mmol) was added by syringe over a 10-min period. The mixture was stirred for 30 min, the ice bath was removed, and the reaction was stirred under nitrogen for 12 h at room temperature. The reaction mixture was then concentrated, dissolved in chloroform, and extracted three times with 1 M $HCl_{(aq)}$. The combined aqueous fractions were treated with a 30 wt % NaOH solution until a pH of 12 was reached. The product was extracted three times with chloroform, and the combined organic fractions were dried over $MgSO_4$ and concentrated. Excess tetraethylene glycol was removed by vacuum distillation, and the residue was purified by column chromatography over silica gel to yield 3.4 g of a colorless oil (40% yield): $^1H$ NMR ($CDCl_3$) δ8.38 (d, 2H), 6.80 (d, 2H), 4.14 (t, 2H), 3.83 (t, 2H), 3.55-3.70 (br m, 12H), 3.08 (br s, 1H); $^{13}C$ NMR ($CDCl_3$) δ164.8, 150.6, 110.3, 72.6, 70.7, 70.2, 69.2, 69.1, 67.1, 61.2; ATR-FTIR 3246, 3036, 2870, 1639, 1591, 1568, 1502, 1454, 1422, 1352, 1284, 1211, 1119, 1051, 1000, 991, 929, 887, 817, 730, 699 $cmm^{-1}$; HPLC (7:3 $H_2O$/aceto-nitrile (0.1% trifluoroacetic acid)) retention time, 1.62 min.

Example 1e

Synthesis of hexaethylene glycol substituted pyridine (2-{2-[2-(2-{2-[2-(Pyridin-4-yloxy)-ethoxy]-ethoxy}-ethoxy)-ethoxy]-ethoxy}-ethanol). To a dry, round-bottom flask was added 4-hydroxypyridine (2.32 g, 24.4 mmol), triphenylphosphine (9.61 g, 36.6 mmol), hexaethylene glycol (8.27 g, 29.3 mmol), and dry THF (125 mL). The mixture was stirred under $N_{2(g)}$ at 0° C. (ice-water bath), and diisopropyl azodicarboxylate (4.96 mL, 25.6 mmol) was added via an addition funnel over a 30 minute period. The mixture was stirred for 30 minutes, the ice bath was removed, and the reaction was allowed to stir under nitrogen for 48 hrs at room temperature. The reaction mixture was then concentrated, dissolved in chloroform, and extracted three times with 1 M $HCl_{(aq)}$. The combined aqueous fractions were treated with a 30 weight percent NaOH solution until a pH of 12 was reached. The product was extracted three times with chloroform, and the combined organic fractions were dried over $MgSO_4$ and concentrated. The product was purified by silica gel chromatography (9:1 $CHCl_3$:MeOH), then dissolved in water and passed through Amberlite® IR-120H ion exchange resin (1 M KOH). The product was extracted three times with $CHCl_3$, the organic fractions combined, dried over MgSO4, and concentrated to a colorless oil: $^1H$ NMR ($CDCl_3$) δ 8.42 (d, 2H), 6.82 (d, 2H), 4.17 (t, 2H), 3.88 (t, 2H), 3.60-3.75 (br m, 20H), 2.70 (br s, 1H).

Example 1f

Synthesis of PEG 550 monomethyl ether-substituted pyridine. To a dry, round-bottom flask was added 4-hydroxypyridine (4.98 g, 52.4 mmol), triphenylphosphine (20.60 g, 78.5 mmol), PEG-550 monomethyl ether (28.8 g, 52.4 mmol), and dry THF (125 mL). The mixture was stirred under $N_{2(g)}$ at 0° C. (ice-water bath), and diisopropyl azodicarboxylate (10.65 mL, 55.0 mmol) was added via an addition funnel over a 30 minute period. The mixture was stirred for 30 minutes, the ice bath was removed, and the reaction was allowed to stir under nitrogen for 12 hours at room temperature. The reaction mixture was then concentrated, dissolved in chloroform, and extracted three times with 1 M $HCl_{(aq)}$. The combined aqueous fractions were treated with a 30 weight percent NaOH solution until a pH of 12 was reached. The product was extracted three times with chloroform, the organic fractions were combined, dried over $MgSO_4$, and concentrated. The crude mixture was purified by silica gel chromatography a colorless oil: $^1H$ NMR ($CDCl_3$) δ 7.34 (d, 2H), 6.30 (d, 2H), 3.89 (t, 2H), 3.72 (t, 2H), 3.47-3.60 (br m, 40.5H), 2.68 (br s, 1H).

Example 2a

Representative synthesis of PEG-substituted ruthenium benzylidene catalyst (compound 4 in Scheme 2, n=2). Tricyclohexylphosphine[1,3-bis(2,4,6-trimethylphenyl)-4,5-dihydroimidazol-2-ylidene][benzylidine]ruthenium (IV) dichloride 3 (50 mg, 0.060 mmol) and PEG-pyridine 2 (320 mg, 0.60 mmol) were combined and diluted in 0.5 mL of dry dichloromethane. The mixture was stirred under nitrogen for 30 minutes. Dichloromethane was removed under vacuum, and the residue was dissolved in methanol. The solid precipitate was filtered leaving a clear, dark green solution. This solution was concentrated and dissolved in water. The aqueous solution was centrifuged for approximately 10 minutes to give a clear, dark green supernatant that was isolated and used directly for metathesis polymerization chemistry.

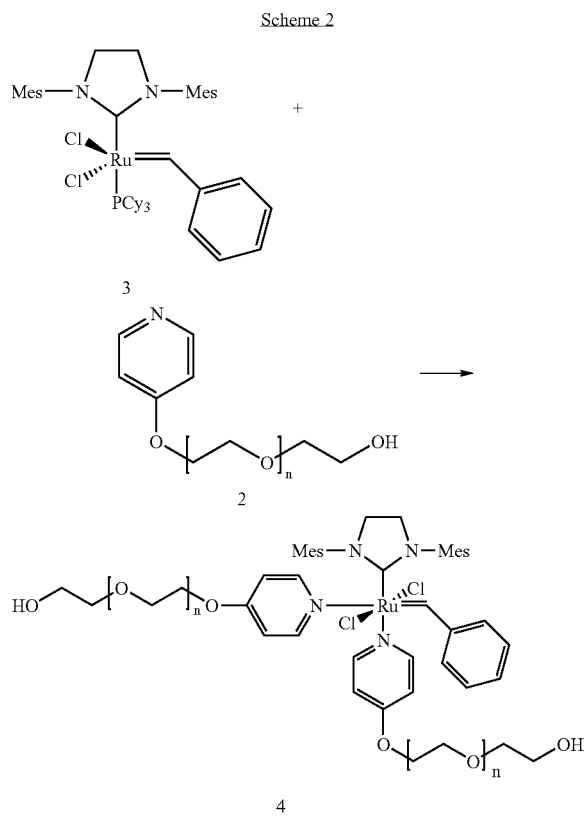

Scheme 2

Catalyst 4 (n≧3) is amphiphilic due to the poly(ethylene glycol) chains. It forms optically clear homogeneous solutions in water, polar protic solvents (e.g., methanol, ethanol, isopropanol, etc.), polar aprotic solvents (e.g., dimethylformamide, dimethylsulfoxide, acetonitrile, etc.), and a variety of organic other organic solvents (eg, acetone, dichloromethane, chloroform, tetrahydrofuran, diethyl ether, toluene, etc). Catalyst 4 is not soluble in hydrocarbon solvents such as pentane, hexane, octane, etc.

Example 2b

Various other catalyst compounds of this invention can be prepared as provided in Example 2a from other such pentavalent Group VIII transition metal (e.g., ruthenium or osmium) complexes known in the art and/or substituted pyridine ligand components, in accordance with this invention. Pentavalent Group VIII complexes useful in preparation of the catalysts of this invention are commercially available from Materia, Inc. or as described in U.S. Pat. No. 6,613,910, the entirety of which is incorporated herein by reference.

Example 2c

Synthesis of Tetraethylene Glycol Substituted Ruthenium Benzylidene Catalyst. With reference to Scheme 2, a solution of compound 3 (50.0 mg, 58.9 μmol) and PEG-pyridine ligand 2, n=3, (0.16 g, 0.59 mmol) in dry dichloromethane (0.3 mL) was stirred under nitrogen for 1 h. Dichloromethane was removed in vacuo, and the remaining green oil was diluted with water to precipitate tricyclohexylphosphine. This aqueous solution was subjected to centrifugation for 5 min to give a clear, dark green, aqueous solution that was removed by a pipette. The green aqueous catalyst solution was concentrated under vacuum (Kügelrohr) to afford a viscous green oil composed of a mixture of 2 and 4. This oil could be diluted in either organic solvents or water for use in ROMP.

$^1$H NMR (CDCl$_3$) δ19.20 (s, catalyst, benzylidene), 8.38 (d, PEG-pyridine ligand), 7.83 (d, catalyst), 7.71 (br s, catalyst), 7.65 (d, catalyst), 7.45 (m, catalyst), 7.33 (m, catalyst), 7.20 (m, catalyst), 7.05 (m, catalyst), 6.94 (t, catalyst), 6.93 (s, catalyst), 6.80 (d, PEG-pyridine ligand), 6.76 (m, catalyst), 6.21 (br s, catalyst), 4.14 (t, PEG-pyridine ligand), 3.83 (t, PEG-pyridine ligand), 3.55-3.70 (br m, PEG-pyridine ligand), 3.18 (m, catalyst), 2.93 (m, catalyst), 2.57, (s, catalyst), 2.15-2.4 (br m, catalyst); $^{31}$P NMR—no signals, indicative of absence of tricyclohexylphosphine.

Example 2d

Alternatively, catalyst compounds of this invention can be prepared from various hexavalent Group VIII transition metal (e.g., ruthenium or osmium) complexes of the type described in U.S. Pat. No. 6,759,537, the entirety of which is incorporated herein by reference. See, e.g., examples 2e and 2f, below, also illustrating catalyst preparation substantially absent excess substituted pyridine ligand.

Example 2e

Synthesis of triethylene glycol substituted ruthenium catalyst. To a dry, two-neck round bottom flask was added (IMesH$_2$)(C$_5$H$_5$N)$_2$(Cl)$_2$Ru═CHPh (0.1041 g, 0.143 mmol), triethylene glycol substituted pyridine (0.065 g, 0.286 mmol), and dry dichloromethane (0.2 mL). The mixture was stirred for thirty minutes and the solvent and pyridine ligand were removed in vacuo. Dry dichloromethane (0.2 mL) was added again, stirred for fifteen minutes, and removed in vacuo. This process was repeated six times, at which point a dark green, amorphous solid was obtained. The catalyst was used without further purification.
$^1$H NMR (CDCl$_3$) δ 19.14 (s, catalyst, benzylidene), 8.44 (d, PEG-pyridine ligand), 7.66 (d, catalyst), 7.60 (d, catalyst), 7.45 (m, catalyst), 7.19 (m, catalyst), 7.16 (m, catalyst), 7.05-7.10 (br m, catalyst), 6.97 (m, catalyst) 6.89 (d, PEG-pyridine ligand), 6.76 (m, catalyst), 6.76 (br s, catalyst), 6.51 (d, catalyst) 4.14 (t, PEG-pyridine ligand), 3.89 (t, PEG-pyridine ligand), 3.55-3.70 (br m, PEG-pyridine ligand), 2.97 (m, catalyst), 2.57, (s, catalyst), 2.2-2.44 (br m, catalyst), 2.17 (s, catalyst)

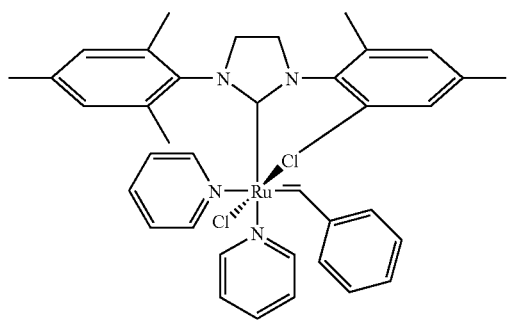

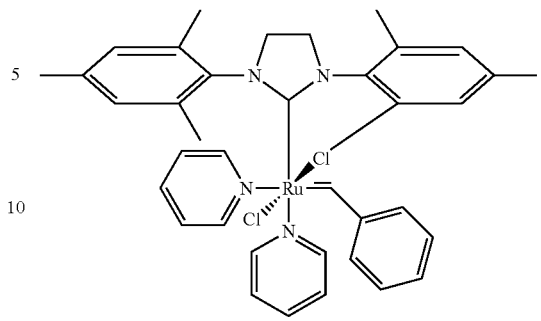

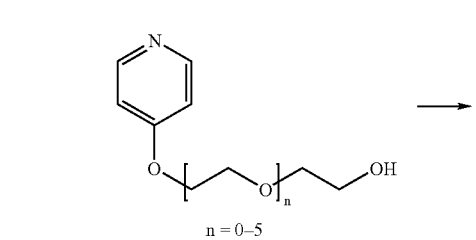

n = 0–5

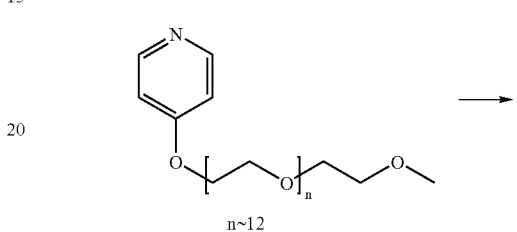

n~12

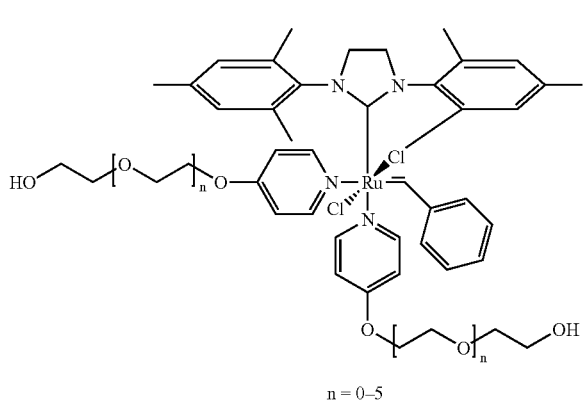

n = 0–5

Example 2f

Synthesis of PEG 550 monomethyl ether substituted ruthenium catalyst. To a dry, two-neck round bottom flask was added (IMesH$_2$)(C$_5$H$_5$N)$_2$(Cl)$_2$Ru=CHPh (0.1667 g, 0.229 mmol), polyethylene glycol 550 monomethyl ether-substituted pyridine (0.2719 g, 0.458 mmol), and dry dichloromethane (0.2 mL). The mixture was stirred for thirty minutes and the solvent and pyridine were removed in vacuo. Dichloromethane (0.2 mL) was added again, stirred for fifteen minutes, and removed in vacuo. This process was repeated six times, at which point a dark green, amorphous solid was obtained. The catalyst was used without further purification. $^1$H NMR (CDCl$_3$) δ 19.17 (s, catalyst, benzylidene), 8.62 (br s, catalyst), 7.81 (br s, catalyst), 7.61 (d, catalyst), 7.47 (t, catalyst), 7.38 (d, PEG-pyridine ligand), 7.06 (t, catalyst), 6.93-7.00 (br m, catalyst), 6.74 (s, catalyst) 6.36 (d, PEG-pyridine ligand), 4.19 (br m, catalyst), 4.03 (br m, catalyst), 3.93 (t, PEG-pyridine ligand), 3.75 (t, PEG-pyridine ligand), 3.53-3.65 (br m, PEG-pyridine ligand), 3.36 (s, catalyst), 2.63 (s, catalyst), 2.22-2.42 (br m, catalyst), 2.1 (br s, catalyst)

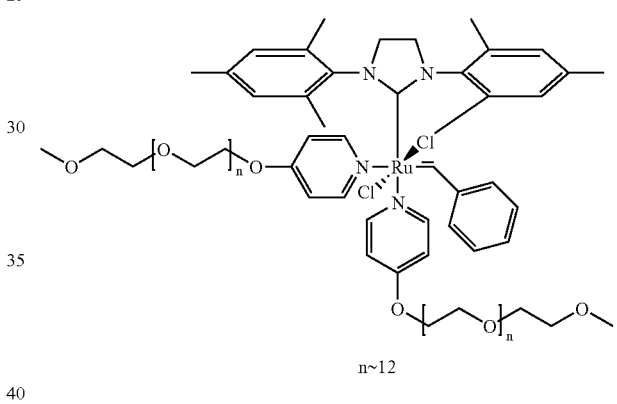

n~12

Example 3

Examples of metathesis chemistry using amphiphilic ruthenium benzylidene catalyst 4. Examples 3a and 3b schematically show polymerization chemistry that can be performed in neutral water using the PEG-substituted ruthenium benzylidene catalysts of this invention. Examples 3c and 3d schematically show small molecule chemistry that can be performed in water with these catalysts, for example cross-metathesis (example 3c) and ring-opening cross-metathesis (example 3d). These important organic transformations are, as a result of this invention, now feasible in neutral water with use of highly active heterocyclic carbene-substituted ruthenium (osmium) benzylidene-type ROMP catalysts. Examples 3e-3g describe, more specifically, use of the amphiphilic catalyst compounds of this invention, as illustrated through the polymerization of representative bicyclic alkenes. (See, FIGS. 1 and 2.)

Example 3a

Ring opening metathesis polymerization of PEG-substituted cyclooctene derivatives in water, where the PEG chain is attached to the cyclooctene derivative by an ether, amide, ester or other linkage.

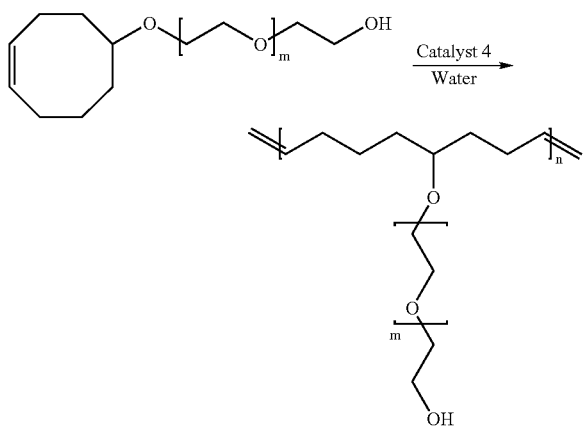

Example 3b

Ring opening metathesis polymerization of oxanorbornene derivative in water

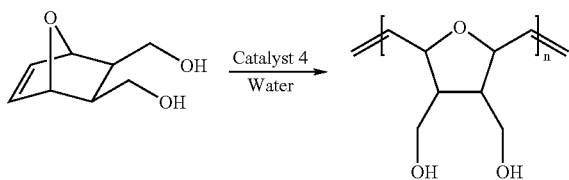

Example 3c

Cross-metathesis reaction in water

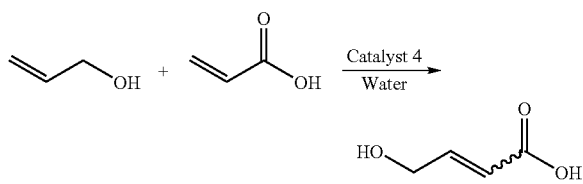

Example 3d

Ring opening cross-metathesis reaction in water

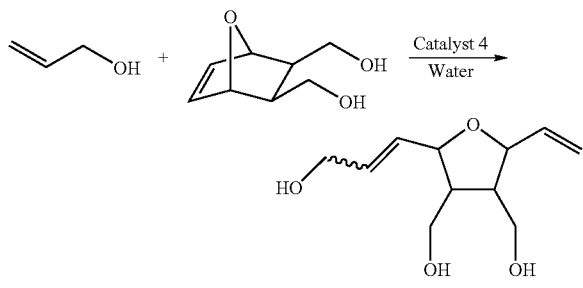

Example 3e

Synthesis of Tetraethylene Glycol Substituted Oxanorbornene 6-(4-(2-{2-[2-(2-Hydroxy-ethoxy)-ethoxy]-ethoxy}-ethyl)-10-oxa-4-aza-tricyclo [5.2.1.0$^{2,6}$]dec-8-ene-3,5-dione). To a dry round-bottomed flask were added the oxanorborne imide, 10-oxa-4-aza-tricyclo[5.2.1.0$^{2,6}$] dec-8-ene-3,5-dione, (3.00 g, 18.2 mmol), triphenylphosphine (5.50 g, 20.9 mmol), tetraethylene glycol (17.6 g, 90.8 mmol), and dry THF (150 mL). (The dione was prepared according to the literature: Kwart et al., JACS, 1952, 74, 3094-3097.) The mixture was stirred under $N_{2(g)}$ at 0° C. (ice-water bath), and diisopropyl azo-dicarboxylate (4.10 mL, 20.9 mmol) was added by syringe over a 10-min period. The mixture was stirred for 30 min. The ice bath was then removed, and the mixture stirred for 12 h at room temperature. The mixture was then concentrated, dissolved in ether, and extracted three times with water. The aqueous fractions were combined, and the product was then extracted from the aqueous phase with chloroform. The chloroform solution was dried over $MgSO_4$ and concentrated, and the product was purified by column chromatography on silica gel using hexane/ethyl acetate mixtures to yield 3.8 g (61% yield) of a viscous, colorless oil.

$^1$H NMR (CDCl$_3$) δ6.48 (s, 2H), 5.23 (s, 2H), 3.55-3.70 (br m, 18H), 2.84 (s, 2H); $^{13}$C NMR (CDCl$_3$) δ176.4, 136.7, 81.0, 72.6, 70.7, 70.6, 70.5, 70.2, 67.3, 61.8, 47.6, 38.3; ATR-FTIR 3458, 2896, 1772, 1694, 1429, 1398, 1336, 1287, 1193, 1096, 1067, 1020, 916, 877, 853, 825, 813, 721, 710 cm$^{-1}$; HPLC (7:3 H$_2$O/acetonitrile (0.1% trifluoroacetic acid)) retention time, 1.99 min.

Example 3f

Ring-Opening Metathesis Polymerization in Dichloromethane. With reference to FIG. 1, exo,exo-5,6-Bis(methoxycarbonyl)-7-oxabicyclo[2.2.1] hept-2-ene (0.2 g, 0.9 mmol) was stirred in dry dichloromethane (1.9 mL) at room temperature under $N_{2(g)}$. A 0.03 M solution (0.64 mL) of catalyst compound 4 (Scheme 2, n=3) in dichloromethane was added rapidly by syringe. The mixture was stirred for 30 min, and ethyl vinyl ether (0.5 mL) was added. Precipitation into cold methanol gave a white solid that was filtered and dried in vacuo to afford 0.17 g (85% yield) of the corresponding polymer.

$^1$H NMR (CHCl$_3$) δ5.89 (m, 1H), 5.62 (m, 2H), 5.05 (br m, 2H), 4.71 (br m, 1H), 3.68 (br m, 6H), 3.08 (m, 2H); GPC (in THF vs. linear polystyrene standards) $M_n$=65,900 g/mol, $M_w$=71,400 g/mol, PDI=1.08.

Example 3g

Ring-Opening Metathesis Polymerization in Water. With reference to FIG. 2 a 0.015 M solution (1.6 mL) of catalyst compound 4 (Scheme 2, n=3) in acidified water (HCl, pH 1.5) was added to 1.3 mL acidified water (HCl, pH 1.5) in a reaction tube, and the mixture was stirred at room temperature under nitrogen. A 0.60 M stock solution (1.0 mL) of tetraethylene glycol substituted oxanorbornene in acidified water (HCl, pH 1.0) was injected rapidly into the catalyst solution, and the mixture was stirred for 30 min. Diethylene glycol vinyl ether was added, and the mixture was then concentrated, dissolved in a minimal amount of CHCl$_3$, and precipitated into cold hexane. The hexane was decanted and the polymer residue dried under vacuum to afford 0.16 g (80% yield) of the corresponding polymer as a tacky solid.

$^1$H NMR (CHCl$_3$) δ6.08 (br s, 1H), 5.78 (br m, 1H), 5.05 (br m, 1H), 4.49 (br m, 1H), 3.55-3.70 (br m, 18H), 2.84 (br s, 2H); GPC (DMF with LiBr (0.05 M) vs. linear poly (methyl methacrylate) standards) $M_n$=67,000 g/mol, $M_w$=90,700 g/mol, PDI=1.35.

Example 4

With reference to examples 5-8, compound 6 can be prepared as shown below, then used with a catalyst compound of this invention en route to interfacial assembly of a nanoparticulate composite comprising cross-linked ligand components.

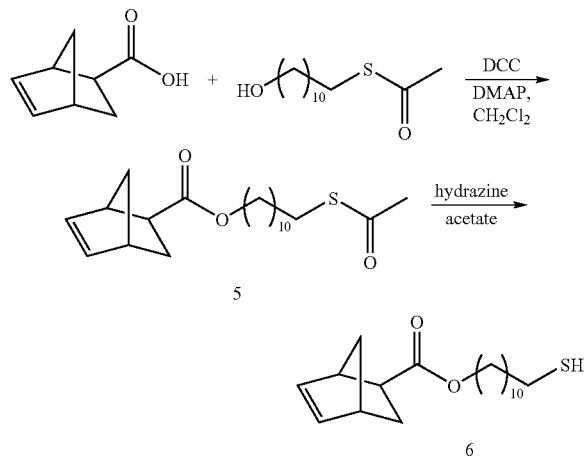

General. Selenium (99.999%) and tri-n-octylphosphine (tech. grade) were purchased from Alfa Aesar. Hexylphosphonic acid (HPA) was purchased from Organometallics, Inc. Cadmium oxide, 5-norbornene-2-carboxylic acid, dicyclohexylcarbidiimide, hexadecylamine, hydrazine acetate and all other reagents were purchased from Aldrich. Tetrahydrofuran and toluene was purified by conventional distillation over sodium/benzophenone and methylene chloride was dried over calcium hydride. $^1$H, $^{13}$C, and $^{31}$P NMR spectra were recorded on a Brüker-Spectrospin 300. Transmission electron microscopy (TEM) was performed on a JEOL JEM-3010. TEM grids were purchased from Ted Pella, Inc. and consisted of 3-4 nm amorphous carbon film supported on a 400-mesh copper grid. Confocal microscopy was performed on a Leica TCS SP2 LSCM with an oil-emersion objective and Ar-laser excitation (excitation: 488 nm, detection: 590 nm).

Example 5

Preparation of compound 5. 5-norbornene-2-carboxylic acid (1.00 g, 7.20 mmol), 11-thioacetate undecanol (2.14 g, 8.70 mmol), dicyclohexylcarbodiimde (1.79 g, 8.70 mmol), and 4-(dimethylamino)pyridine (0.53 g, 4.40 mmol) were dissolved in CH$_2$Cl$_2$ (20 mL). The reaction was stirred at room temperature under an inert atmosphere for 1 hr. The reaction mixture was filtered and the solvent was removed under reduced pressure to give a viscous liquid. The product was purified by column chromatography eluting with CHCl$_3$:hexane mixtures to yield 1 (1.93, 89%). $^1$H NMR (300 MHz, CDCl$_3$) δ 6.20-5.91 (m, 2H), 4.04 (m, 2H), 3.21 (br s, 1H), 2.91 (m, 4H), 2.32 (s, 3H), 1.94-1.2 (m, 24H) ppm; $^{13}$C NMR (75 MHz, CDCl$_3$) δ 196.0, 174.8, 138.0, 132.3, 64.5, 64.3, 55.7, 49.6, 46.6, 46.3, 45.7, 43.3, 43.2, 42.5, 41.6, 34.9, 30.6, 30.3, 29.5, 29.4, 29.3 ppm.

Example 6

Preparation of compound 6. Compound 5 (1.0 g, 2.7 mmol) was dissolved in DMF (15 mL) and stirred at room temperature under an inert atmosphere. Hydrazine acetate (0.75 g, 8.1 mmol) was added to the solution and allowed to react for 20 min. The reaction mixture was filtered and the solvent was removed under reduced pressure to yield (0.68 g, 97%). $^1$H NMR (300 MHz, CDCl$_3$) δ 6.20-5.91(m, 2H), 4.02 (m, 2H), 3.21 (br s, 1H), 2.89 m, 4H), 2.50 t, 2H), 2.30 (br, 1H), 1.63-1.26 (m, 20H) ppm; $^{13}$C NMR (75 MHz, CDCl$_3$) δ 174.8, 138.0, 132.3, 64.3, 46.6, 46.3, 45.7, 43.3, 43.1, 42.5, 41.6, 34.0, 29.4, 29.1, 29.0, 28.6, 28.3, 25.9, 24.6 ppm.

Example 7

Preparation of 6-functionalized CdSe/ZnS nanoparticles. TOPO-covered CdSe/ZnS nanoparticles were prepared as described in the literature. Chen, Y. F.; Ji, T. H.; Rosenzweig, Z. Nano Letters 2003, 3, 581. The particles were dissolved in pyridine and refluxed overnight under an inert atmosphere. The pyridine was partially removed under reduced pressure to give a viscous solution. The nanoparticles were precipitated by the addition of hexane and centrifuged. The supernate was discarded, and the precipitate (ca. 20 mg CdSe nanoparticles) was stirred as a suspension in freshly distilled, dry THF. Compound 6 (ca. 150 mg) was added, and the suspension was stirred for several hours at 50° C. The THF was partially removed by distillation, and the remaining solution was precipitated with anhydrous methanol and centrifuged. The supernate was again discarded, and the 6-covered nanoparticles were dissolved in freshly distilled toluene (7 mL). Other nanoparticulate substrates, either commercially-available or as known in the art, can be used, accordingly or with various other coupled alkenes, with comparable effect.

Example 8

General procedure for the preparation of cross-linked nanoparticle composites. 300 μL of 6-functionalized CdSe/ZnS nanoparticles (ca. 2 mg/1 mL) in toluene and 25 μL of ethyl vinyl ether were added to a eppendorf tube. 25 μL aqueous solution of catalyst 5 (1 mg/1 mL) was added to the nanoparticle solution and shaken vigorously. The nanoparticle capsules were allowed to settle to the bottom of the solution and the excess nanoparticle solution was removed and fresh toluene was added.

TEM was performed by transferring the cross-linked nanoparticle capsules to TEM grids and allowing the capsules to dry. A low magnification TEM image, shown in FIG. 3A, demonstrates that the spherical nature of the capsule was maintained following drying, an observation consistent with successful cross-linking. Moreover, the close-packed liquid-like nature of the nanoparticles, while expected from prior studies, is confirmed by the higher-magnification TEM image of FIG. 3B.

While several principles relating to this invention have been described in connection with specific embodiments, it should be understood clearly that these descriptions are added only by way of example and are not intended to limit, in any way, the scope of this invention. For instance, as metathesis reactions become increasingly useful in drug synthesis, water soluble catalyst compounds of this invention will find increasing use in the reaction of polar compounds, thereby reducing risk of contamination by organic solvents. More generally, the utility of such catalyst compounds and aqueous and/or polar media, can provide access to functional amphiphilic and/or water soluble polymers not otherwise attainable through conventional polymerization techniques. As such, the present invention represents a divergent class of Group VIII catalyst compounds and their extension to chemistries and products not available through the prior art.

We claim:

1. A Group VIII transition metal compound of a formula

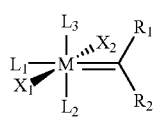

wherein M is a metal selected from a Group VIII transition metal; $X_1$ and $X_2$ are independently selected from anionic ligand components; $L_1$-$L_3$ are independently selected from neutral electron donor ligand components, providing one of said $L_1$-$L_3$ components is an N-heterocyclic carbene component and the other said $L_1$-$L_3$ components are independently selected from amphiphilic substituted pyridinyl ligand components, said amphiphilic substituent comprising at least one of an alkoxy moiety and an alkoxycarbonyl moiety; and $R_1$—$R_2$ are independently selected from hydrogen, alkyl, substituted alkyl, cyclic alkyl, substituted cyclic alkyl, alkenyl, substituted alkenyl, cyclic alkenyl, substituted cyclic alkenyl, phenyl and substituted phenyl moieties.

2. The compound of claim 1 wherein at least one of said pyridinyl ligand components comprises a polyalkoxy substituent.

3. The compound of claim 2 wherein said substituent comprises $(OCH_2CH_2)_n$, and n ranges from about 2 to about 100.

4. The compound of claim 1 wherein M is selected from Ru and Os.

5. The compound of claim 4 wherein $R_1$ is hydrogen and $R_2$ is phenyl.

6. A metathesis catalyst compound of a formula

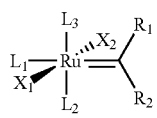

wherein $X_1$ and $X_2$ are independently selected from anionic ligand components; $L_1$-$L_3$ are independently selected from neutral electron donor ligand components, providing one of said $L_1$-$L_3$ components is an N-heterocyclic carbene component and the other said $L_1$-$L_3$ components are independently selected from amphiphilic substituted pyridinyl ligand components, said amphiphilic substituent comprising at least one of an alkoxy moiety and an alkoxycarbonyl moiety; and $R_1$—$R_2$ are independently selected from hydrogen, alkyl, substituted alkyl, cyclic alkyl, substituted cyclic alkyl, alkenyl, substituted alkenyl, cyclic alkenyl, substituted cyclic alkenyl, phenyl and substituted phenyl moieties.

7. The compound of claim 6 wherein at least one of said pyridinyl ligand components comprises a polyalkoxy substituent.

8. The compound of claim 7 wherein said substituent comprises $(OCH_2CH_2)_n$, and n ranges from about 2 to about 100.

9. The compound of claim 6 wherein said carbene ligand component comprises a 4,5-dihydroimidazolylidene moiety.

10. The compound of claim 9 wherein $R_1$ is hydrogen and $R_2$ is phenyl.

11. A reaction system comprising an amphiphilic compound of claim 6 and at least one alkene compound.

12. The system of claim 11 comprising two acyclic alkene compounds, said system for a cross-metathesis reaction.

13. The system of claim 12 comprising a cyclic alkene compound and an acyclic alkene compound, said system for a ring-opening cross-metathesis reaction.

14. The system of claim 11 comprising a cyclic alkene compound, said system for a ring-opening metathesis polymerization reaction.

15. The system of claim 14 wherein said alkene compound is coupled to a substrate.

16. The system of claim 15 wherein said substrate is a nanodimensioned particulate.

17. The system of claim 15 wherein said alkene compound is cross-linked with another said alkene compound coupled to said substrate.

18. The system of claim 17 wherein said nanodimensional particulate comprises a semiconductive, luminescent material.

19. A method of using an N-heterocyclic carbene ruthenium benzylidene catalyst for a ring-opening metathesis reaction in an aqueous medium, said method comprising:
providing a cyclic alkene compound; and
contacting said alkene compound and a catalyst compound of claim 6, said catalyst compound wherein $R_2$ is phenyl, said contact for a time sufficient for reaction of said alkene compound, at least one of said alkene and said catalyst compounds in an aqueous medium.

20. The method of claim 19 wherein at least one of said pyridinyl components comprises a polyalkoxy substituent.

21. The method of claim 20 wherein said substituent comprises $(OCH_2CH_2)_n$, and n ranges from about 2 to about 100.

22. The method of claim 19 wherein said carbene ligand component of said catalyst compound comprises a 4,5-dihydroimidazolylidene moiety.

23. The method of claim 19 wherein said alkene component is coupled to a substrate component.

24. The method of claim 23 wherein said coupled components are provided in a substantially hydrophobic medium, said catalyst compound in an aqueous medium, said contact for a time sufficient to cross-link said alkene compound.

* * * * *

UNITED STATES PATENT AND TRADEMARK OFFICE
CERTIFICATE OF CORRECTION

PATENT NO.        : 7,332,609 B2
APPLICATION NO. : 11/254947
DATED             : February 19, 2008
INVENTOR(S)       : Todd S. Emrick and Kurt Breitenkamp It is certified that error appears in the above-identified patent and that said Letters Patent is hereby corrected as shown below:

Col. 3, Line 3 "(F-caprolactone)" should be -- ε-caprolactone --;

Col. 7, Line 17 "Bronstead" should be -- Brønstead --;

Col. 9, Line 50 "Bruker" should be -- Brüker --;

Col. 17, Line 15 "$m$" should be -- 3 --

Signed and Sealed this

Twelfth Day of August, 2008

JON W. DUDAS
*Director of the United States Patent and Trademark Office*